United States Patent
Steiner et al.

(10) Patent No.: US 6,669,701 B2
(45) Date of Patent: Dec. 30, 2003

(54) BONE PLATE

(75) Inventors: Béatrice Steiner, Cham (CH); Markus Hehli, Frauenkirch (CH); Max Aebi, Montreal (CA); Thomas Steffen, Montreal (CA)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/994,050

(22) Filed: Nov. 27, 2001

(65) Prior Publication Data

US 2002/0183752 A1 Dec. 5, 2002

Related U.S. Application Data

(63) Continuation of application No. PCT/CH00/00037, filed on Jan. 27, 2000.

(51) Int. Cl.$^7$ ............................................. A61B 17/80
(52) U.S. Cl. ........................... 606/69; 606/71; 606/72; 606/73
(58) Field of Search ........................... 606/69, 70, 71, 606/72, 73

(56) References Cited

U.S. PATENT DOCUMENTS

| | | | |
|---|---|---|---|
| 3,552,389 A | 1/1971 | Allgower et al. | 128/92 |
| 3,668,972 A | 6/1972 | Allgower et al. | 90/11 C |
| 3,716,050 A | 2/1973 | Johnston | 128/92 |
| 3,779,240 A | 12/1973 | Kondo | 128/92 |
| RE28,841 E | 6/1976 | Allgower et al. | 128/92 |
| 4,219,015 A | 8/1980 | Steinemann | 128/92 |
| 4,408,601 A | 10/1983 | Wenk | 128/92 D |
| RE31,628 E | 7/1984 | Allgower et al. | 128/92 |
| 4,493,317 A | 1/1985 | Klaue | 128/92 |
| 4,513,744 A | 4/1985 | Klaue | 128/92 |
| 4,927,421 A | 5/1990 | Goble et al. | 606/73 |
| 5,002,544 A | 3/1991 | Klaue et al. | 606/69 |
| 5,006,120 A | 4/1991 | Carter | 606/69 |
| 5,304,180 A | 4/1994 | Slocum | 606/69 |
| 5,601,553 A | 2/1997 | Trebing et al. | 606/61 |
| 5,702,399 A | 12/1997 | Kilpela et al. | 606/72 |
| 5,709,686 A | 1/1998 | Talos et al. | 606/69 |
| 5,810,823 A | 9/1998 | Klaue et al. | 606/69 |
| 5,938,664 A | 8/1999 | Winquist et al. | 606/69 |
| 6,183,475 B1 | 2/2001 | Lester et al. | 606/69 |

FOREIGN PATENT DOCUMENTS

| | | | |
|---|---|---|---|
| CH | 611147 | 5/1979 | ............ A61B/17/18 |
| DE | 43 41 980 A | 6/1995 | |
| DE | 43 43 117 A | 6/1995 | |
| DE | 4438264 A1 | 3/1996 | ............ A61B/17/70 |
| EP | 0 207 884 A2 | 1/1987 | ............ A61B/17/58 |
| WO | WO 97/09000 | 3/1997 | |

Primary Examiner—Cary E. O'Connor
Assistant Examiner—Candice C. Melson
(74) Attorney, Agent, or Firm—Pennie & Edmonds, LLP

(57) ABSTRACT

A bone plate includes an upper surface, a bone contacting surface, and at least one hole extending through the upper and bone contacting surfaces for receiving a bone screw. The at least one hole includes a first portion and a second portion that overlap one another. The first portion defines a substantially circular outer periphery and the second portion defines an elongated outer periphery that is elongated in a direction substantially parallel to the longitudinal axis of the plate. The first portion may have threads configured to engage threads on the head of a bone screw, and the second portion may be configured to cooperate with the head of a different bone screw to provide compression to the fracture.

27 Claims, 4 Drawing Sheets

BONE PLATE

CROSS-REFERENCE TO RELATED APPLICATIONS

The present application is a continuation of the U.S. National Stage designation of co-pending International Application PCT/CH00/00037, filed Jan. 27, 2000, the entire content of which is expressly incorporated herein by reference thereto.

TECHNICAL FIELD OF THE INVENTION

The present invention relates generally to devices for fixation of parts of a fractured bone and more specifically, to bone plates and systems for stabilization and/or compression of parts of a fractured bone.

BACKGROUND OF THE INVENTION

Bone plates may generally be utilized to carry out two different types of osteosynthesis, namely "rigid osteosynthesis" and "flexible osteosynthesis." Rigid osteosynthesis is used for medical care of joint fractures, simple shaft fractures (where nailing is impossible) as well as for osteotomies. Aside from the possibility of anatomical repositioning, the bone itself supports and stabilizes the osteosynthesis, which allows for the possibility of putting stress on the extremity earlier and without pain. Additional advantages of the medical care of stable fractures can be observed when the blood circulation in the bone is greatly diminished due to trauma. For treating "nonunions" or in the case of existing infection, the fracture must be kept stable in order to make bone healing possible and so as not to irritate the infection further by instability of the fracture gap.

Flexible osteosynthesis, also known as "biological osteosynthesis," may be desirable in the medical treatment of comminuted fractures in the shaft region of tubular bones. In the case of these fractures, it is an objective to maintain the proper length of the bone and to fix the bone ends (joints) in their proper anatomic positions with respect to one another. With flexible osteosynthesis, the fracture zone is not directly affixed or manipulated, and consequently, the blood circulation in this area is not inhibited. Bone plates designed for flexible osteosynthesis thus operate similarly to a locking, intramedullary nail, which is anchored only in the metaphyses.

Since fractures cannot always be treated with one type of osteosynthesis, surgeons must frequently compromise because a bone plate, which allows him to combine the two types of osteosynthesis discussed above, is not available. Such a combination would be beneficial, for example, when a joint fracture can be compressed with traction screws through the bone plate and the whole of the joint may be connected to the diaphysis over an internal fixative with angularly stable screws. Another illustrative application concerns porotic bones, where a bone plate with axially and angularly stable screws can be anchored in the metaphysial fragment, with a stable plate-affixation being undertaken in the diaphyseal range with the assistance of a plate traction screw through the fracture. A primary fracture stabilization can be achieved by this type of procedure.

This situation has led to the development and marketing of bone implants for both types of osteosynthesis. The two types of implants, however, are designed specifically for their respective method. Thus, the disadvantages of these two systems lie in the difficulty in combining them.

Thus, a need exists for improved bone plates that provide for both rigid and flexible osteosynthesis.

SUMMARY OF THE INVENTION

The present invention is directed to a bone plate that is adapted to be used for both rigid and flexible osteosynthesis, without compromising the ability of the plate to be used for either type of osteosynthesis. Accordingly, the bone plate of the present invention may be used as a compression plate or as an internal fixative.

This objective is accomplished with a bone plate having at least one "combination hole." The combination hole may be used with a screw having a substantially spherical head to provide for compression of the fracture, or may be used with a screw having a threaded head to fix the position of the screw with respect to the bone plate and serve as an internal fixative.

The combination hole includes a first portion and a second portion that at least partially overlap one another. The first portion may be substantially circular, and the second portion may be elongated. Within the scope of the invention, the second portion (elongated portion) may have a diametrical dimension that is greater in one direction than in another. For example, the diameter of the elongated portion may be greater in the direction of the longitudinal axis of the plate than in the direction substantially perpendicular to the longitudinal axis. Thus, the elongated portion may be oval, elliptical, rectangular or any other elongated shape known to one of ordinary skill in the art, including combinations of these shapes. The diameter (D) of the first portion (circular portion) may be smaller than the minor (or shortened) axis (B) of the second portion (elongated portion). Typically, diameter (D) is between about 5% and about 25% smaller than the minor axis (B).

According to another aspect of the invention, the circular portion of the hole may be configured and dimensioned to engage the head of a bone screw. More specifically, the circular portion may be provided with an internal thread or a peripheral lamella or lip that may engage a corresponding structure formed on the screw-head. In the case where an internal thread is provided, the thread may be disposed in a single plane, or in several planes. The plane(s) may be parallel to the upper and/or bone contacting surfaces of the bone plate. According to one embodiment, the internal thread may extend over the whole height of the bone plate from the bone contacting surface to the upper surface. This configuration provides increased stability of the bone plate/screw-head interface.

With the threaded screw-head engaged in the threads of the first portion, the bone plate may be used as an internal fixative. Use in this configuration, however, creates high stresses at the interface of the bone plate and screw-head because the plate is not forced against the bone, and therefore, the bone fracture is fixed primarily by friction between the plate and the bone. This increase in stress is taken into account by the threaded portion of the hole extending over a range of at least about 180° with respect to a central axis of the hole, and thereby enclosing the screw-head in at least this angular range. This feature of the bone plate is especially advantageous where thin bone plates are involved. Preferably, the threaded portion is disposed on one of the two longitudinal ends of the hole. This positioning allows for the threaded portion to extend over a larger angular range. For example, the threaded portion may extend over a range of between about 190° and about 280°, and preferably over a range of between about 200° to 250°, thus maximizing the strength of the bone screw to bone plate interface.

According to another embodiment of the invention, the internal thread may be tapered (i.e., formed on the inner surface of a hole that tapers with respect to its central axis). Preferably, the internal thread tapers radially inward toward the bone contacting surface of the bone plate. A bone screw to be rigidly fixed to the bone plate may include a screw-head having a tapered external thread (i.e., formed on an outer surface of the screw-head that tapers with respect to the central axis of the screw-head) that is tapered to match the shape of the tapered internal thread. The bone screw may be rigidly fixed to the bone plate by engagement between the matching threads. This method of attachment is especially advantageous when self-drilling screws are to be used since, due to the tapered shape of the matching threads, the screw may be inserted into the bone independently of the plate. More specifically, the screw-head becomes rigidly clamped to the plate only as the threaded screw-head penetrates the threaded portion of the hole. Despite any initial misalignment between the threads on the screw-head (the position of which are initially dictated by the orientation of the bone screw in the bone) and the threads on the bone plate, the tapered shape of the mating threads ensures that the threads on the screw-head will ultimately align with the threaded portion of the hole. When the tapered thread of the screw-head is tightened into the internal thread of the hole, the screw-head creates radial forces in the plate hole. Thus, the bone plate must be dimensioned and configured to withstand these high radial forces, e.g., to withstand flexing of the walls of the screw holes in the bone plate.

According to one embodiment, the inner thread conically tapers at a cone angle of between about 5° and about 20°. Preferably, the thread tapers at a cone angle of about 10°.

In the case where the inner thread is tapered, as discussed above, the thread may extend through a different angle when measured at the upper surface than when measured at the bone contacting surface. For example, when measured at the upper surface, the inner thread may extend through a first angle of between about 180° and about 230°, while when measured at the bone contacting surface, the inner thread may extend through a second angle of between about 230° and about 270°.

The first portion of the hole, and consequently the inner thread (if provided), may be oriented closer to the center or intermediate portion (as distinguished from the ends) of the plate than the second portion, thus avoiding any undesirable effects on the compression capability of the second portion. Thus, when the bone plate is used as a compression plate, the geometry of the second portion (compression portion) is not adversely affected by the presence of the internal thread.

According to another aspect of the present invention, at least one of the holes may be dimensioned and configured to receive a substantially spherical head of a bone screw and provide for compression of the fractured bone fragments. For example, according to one embodiment, the second portion of the elongated hole, discussed above, may include a concave, substantially spherical recess at the upper surface. The recess may be dimensioned and configured to accommodate the spherical head of a conventional bone screw. Such an arrangement may be especially useful when the bone screw is put in place eccentrically with respect to the hole, as is necessary for attaining compression of a fracture. Additionally, the second portion of the hole may flare outward in the area of the bone contacting surface to provide for increased angulation of the bone screw with respect to the bone plate.

According to another embodiment of the invention, the underside of the bone plate may be concave, thus allowing the plate to conform to the rounded cross-section of the tibia, femur, humerus, forearm bone, and other bones with which the present invention may be used. The concave configuration of the underside also allows a conventional bone screw to be inserted obliquely through the plate hole. This feature may be especially important when gripping a small bone fragment, which must be pulled against the plate.

The present invention is also directed to a bone plating system including at least one bone screw. The bone screw may have a screw-head that is configured and dimensioned to engage the circular portion of the above-described combination hole. For example, the screw-head may include a plurality of external threads disposed thereon that engage the internal threads of the bone plate.

BRIEF DESCRIPTION OF THE DRAWINGS

To facilitate an understanding of the characteristics, structure and operation of the invention, preferred features of the invention are described in the accompanying discussion, wherein similar reference characters denote similar elements throughout the several views or embodiments, and wherein.

DETAILED DESCRIPTION OF THE PREFERRED EMBODIMENTS

Figure 1:
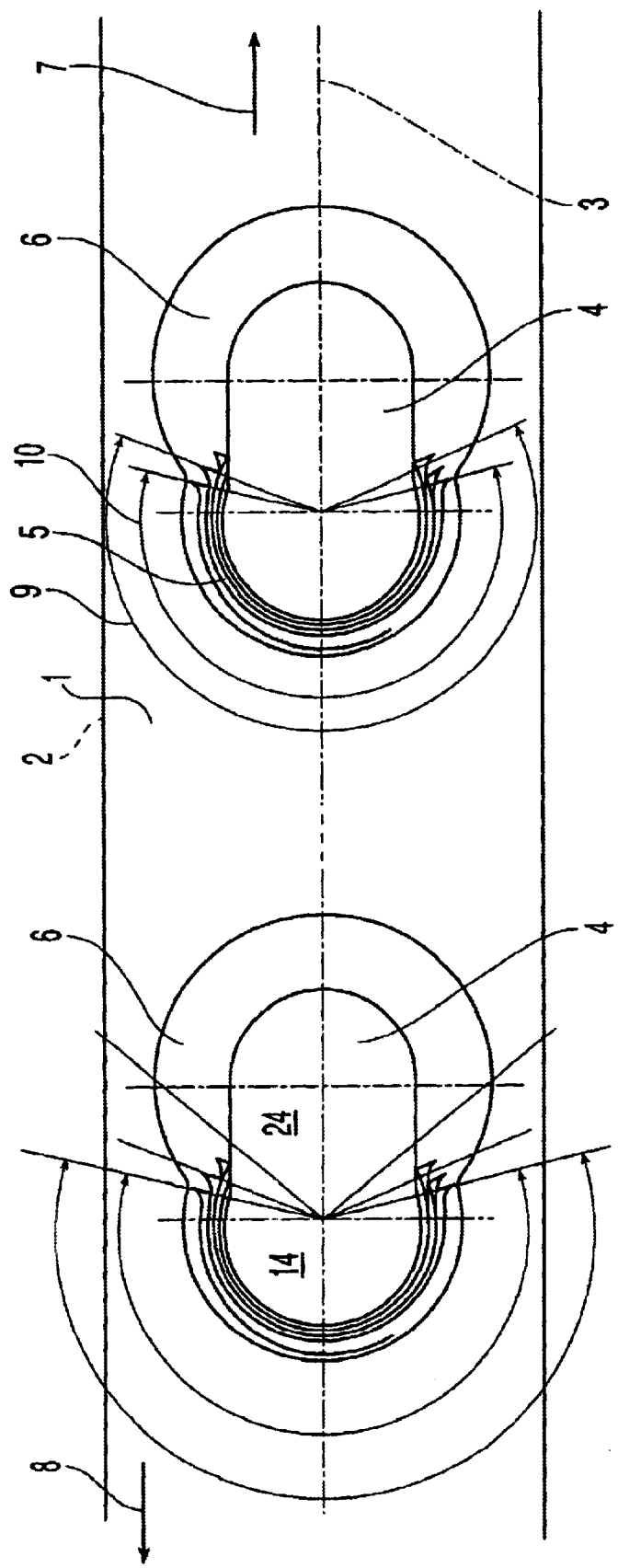
FIG. 1 is a top view of a segment of an illustrative embodiment of a bone plate according to the present invention.
Figure 2:
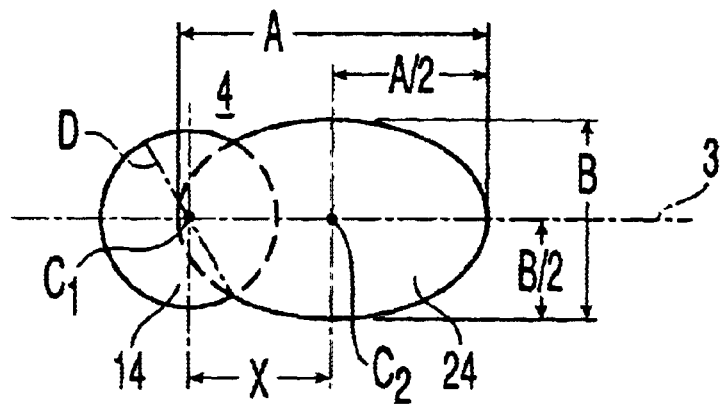
FIG. 2 is a schematic representation of a combination hole of the bone plate of FIG. 1.

One embodiment of a bone plate according to the present invention is shown in FIG. 1. The bone plate defines a longitudinal axis 3, and includes an upper surface 1 and a bone contacting surface 2 intended for contact with the bone. At least one combination hole 4 extends through the upper surface 1 and the bone contacting surface 2. Hole 4 may receive a bone screw 11 that is used to hold the bone plate on the fractured bone. While two holes 4 are shown, the bone plate may be provided with any number of holes 4 as may be suitable for a specific surgical application. In addition, holes 4 may be disposed along the longitudinal axis 3 as shown in FIG. 2, however, holes 4 may alternatively be spaced from the longitudinal axis 3. One of ordinary skill in the art will know and appreciate that the bone plate may be provided with other types and configurations of holes in addition to combination hole 4. For example, the bone plate may be provided with substantially cylindrical holes, threaded holes, or any other type of hole known to one of ordinary skill in the art. The arrow 7 indicates the direction toward one end of the plate, while the arrow 8 indicates the direction toward the center of the plate.

As shown schematically in FIG. 2, the combination hole 4 consists of a first, substantially circular portion 14, and a second, elongated portion 24. The circular portion 14 and the elongated portion 24 overlap one another, and are thus in communication with one another. The outer periphery of circular portion 14 defines a first center point $C_1$, and a diameter D. The outer periphery of elongated portion 24 defines a second center point $C_2$. The outer periphery of elongated portion 24 also defines a major axis A and a minor axis B substantially perpendicular to the major axis A. According to one embodiment of the invention, major axis A may be substantially parallel to longitudinal axis 3 of the bone plate. In addition, major axis A may lie on longitudinal axis 3 with first and second center points $C_1$, $C_2$ located on longitudinal axis 3, however other configurations are possible.

Still referring to FIG. 2, first center point $C_1$ and second center point $C_2$ are separated from one another by a distance X, which may be less than the sum of D/2 and A/2. Preferably, distance X satisfies the following condition:

$$0.5(D/2+A/2) < X < 1.0(D/2+A/2)$$

According to another embodiment, diameter D is less than minor axis B. Preferably, diameter D satisfies the following condition:

$$0.75B \leq D \leq 0.95B$$

Figure 3:
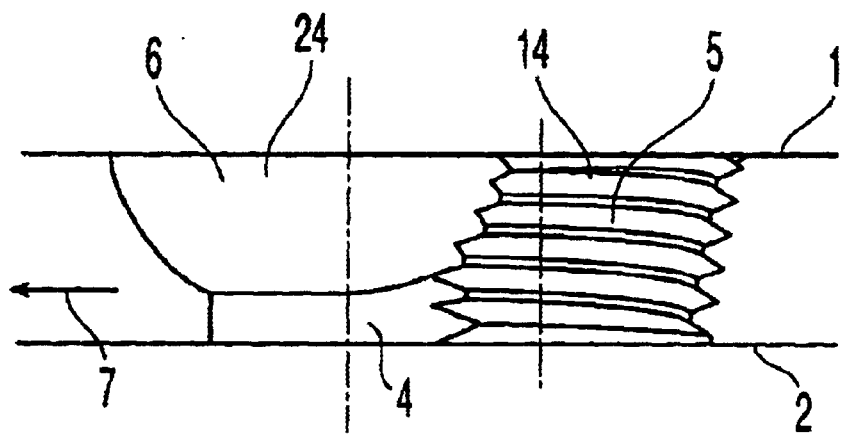
FIG. 3 is a longitudinal cross-sectional view of a portion of the bone plate of FIG. 1, taken through one of the combination holes.

Elongated portion 24 may be configured and dimensioned to receive a substantially spherical screw-head. As shown in FIGS. 1 and 3, elongated portion 24 may have a concave, substantially spherical recess 6 that opens toward upper surface 1 of the bone plate. When the shaft of a bone screw having a spherical head is located eccentrically in elongated portion 24 (towards the left in FIG. 3), the spherical head may engage recess 6 and bias the bone plate to provide compression of the bone fracture.

Still referring to FIG. 3, circular portion 14 may be configured and dimensioned to engage a threaded head of a bone screw. As shown, an internal thread 5 may be provided on circular portion 14. Thread 5 may be disposed in a single plane, or in several planes. The plane(s) may be parallel to upper surface 1 and/or bone contacting surface 2. According to the embodiment shown, thread 5 extends substantially over the entire height of the bone plate from the upper surface 1 to the bone contacting surface 2. In the case where thread 5 is provided, it is preferably oriented at the end of hole 4 that is closest to the center of the bone plate.

With reference to FIG. 1, when measured at upper surface 1, thread 5 extends over a first angle 9 of about 256° with respect to center $C_1$ of circular portion 14, and when measured at bone contacting surface 2, thread 5 extends over a second angle 10 of about 223° with respect to center point $C_1$. One of ordinary skill in the art will know and appreciate, however, that other values of first angle 9 and second angle 10 are possible.

The table below displays, for illustrative purposes only, preferred parameters which may be used for thread 5.

| Thread Diameter [mm] | 2.4 | 3.5 | 5.0 |
|---|---|---|---|
| Double Thread | Yes | Yes | Yes |
| Lead [mm] | 0.6 | 0.8 | 1.0 |
| Thread Depth [mm] (defined as approximately half the difference between the external and internal thread) | 0.175 | 0.2295 | 0.2810 |
| Angular Range (at upper surface) | 200° | 200° | 190° |
| Angular Range (at bone contacting surface) | 260° | 204° | 250° |

Figure 5:
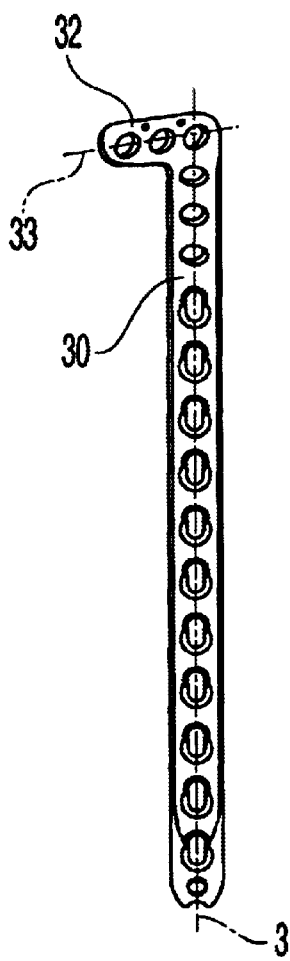
FIG. 5 is a top view of a substantially L-shaped bone plate according to the present invention.
Figure 6:
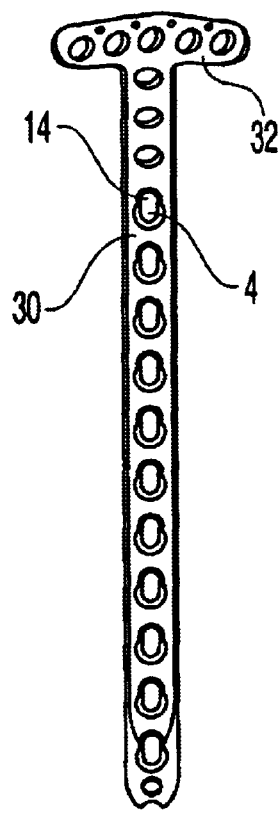
FIG. 6 is a top view of a substantially T-shaped bone plate according to the present invention.
Figure 7:
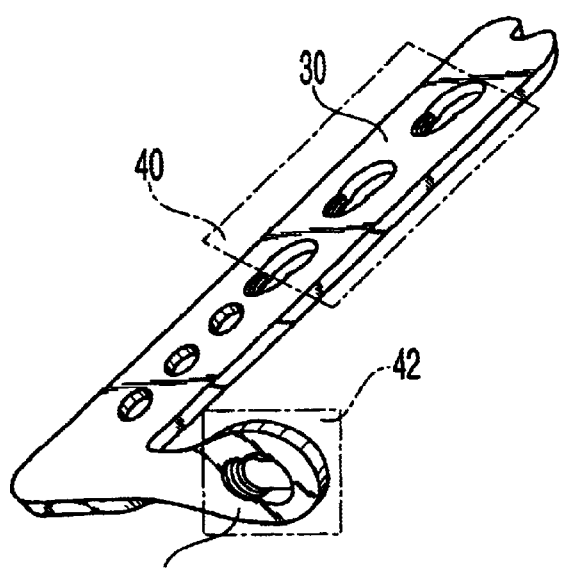
FIG. 7 is a perspective view of the bone plate of FIG. 5.

The bone plate may include multiple sections having longitudinal axes that are The bone plate may include multiple sections having longitudinal axes that are oriented with respect to one another in order to fit a particular medical application. Referring now to FIG. 5, according to one embodiment, the bone plate may include a first section 30 that, as described above, has a first longitudinal axis 3, and a second section 32 that similarly has a second longitudinal axis 33. As shown, the first and second longitudinal axes 3, 33 may be angled with respect to one another. In addition, the first and second sections 30, 32 may have different lengths, e.g., the first section may be longer than the second section. For example, the bone plate may be substantially T-shaped, as shown in FIG. 6, or L-shaped, as shown in FIG. 5, although other configurations are possible. The sections may also be located in different planes. For instance, as shown in FIG. 7, the plate may be bent or twisted such that the bone contacting surface of the first section 30 is located in a first plane 40 and the bone contacting surface of the second section 32 is located in a second plane 42 different from the first plane 40. This may be beneficial where the bone plate has to be located over a curved portion of a bone, such as the femoral head.

In the case where one section is longer than another, at least one combination hole 4 is preferably located on the longer section and oriented with the first portion 14 of the hole 4 located closer to the shorter section than the second portion 24 of the hole 4. Thus, in the case of a T-shaped plate, shown in FIG. 6, the hole 4 would preferably be disposed on the first, longer section 30 of the plate with the first portion 14 oriented closer to the second, shorter section 32.

Figure 4:
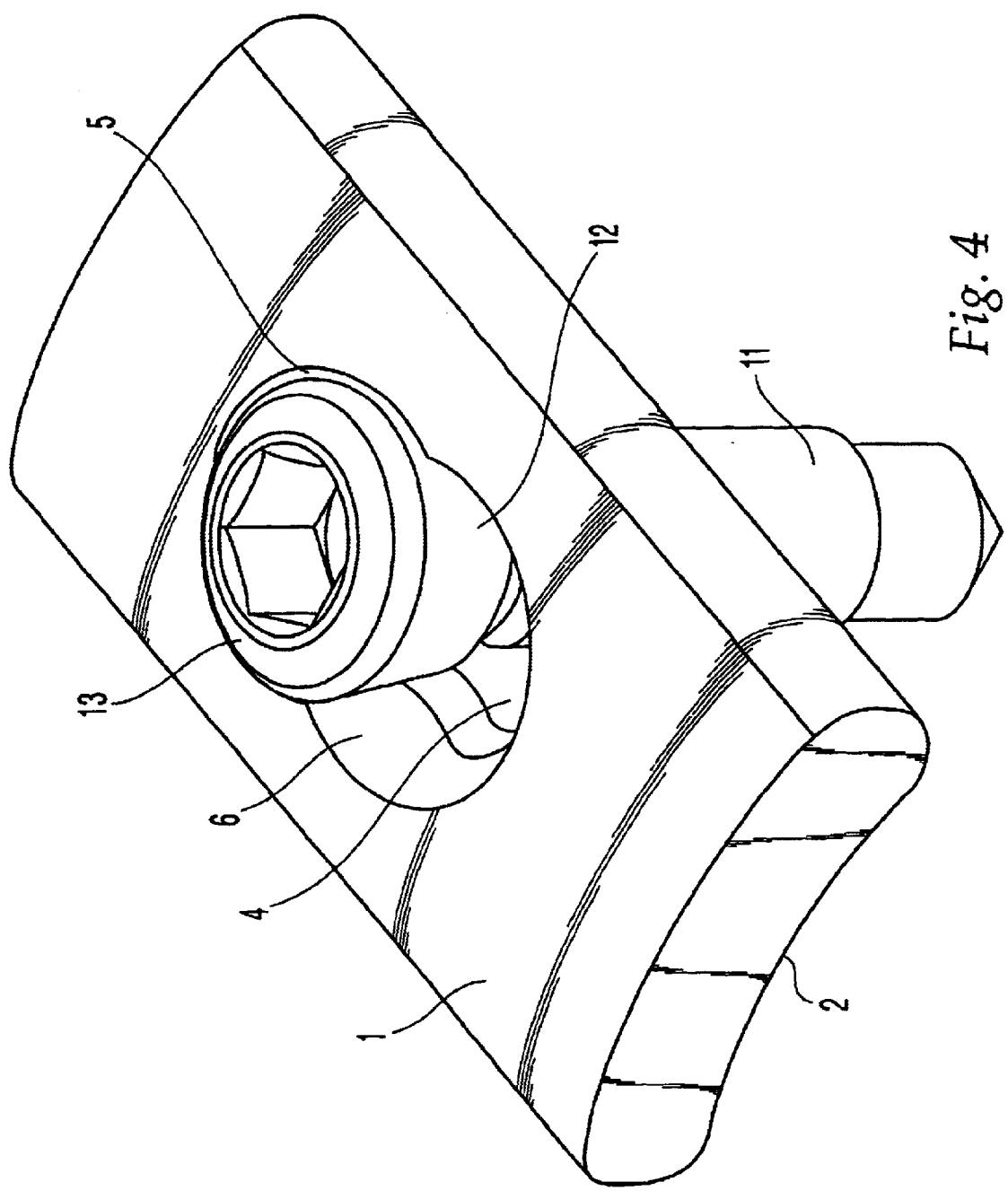
FIG. 4 is a perspective view of a portion of the bone plate of FIG. 1, shown with a bone screw inserted in one of the combination holes.

Referring to FIG. 4, combination hole 4 is shown with a bone screw 11 received therein. The head 13 of the bone screw 11 preferably has one or more threads 12 disposed thereon. Threads 12 of the bone screw 11 may mate with threads 5 of hole 4, to fix the position of bone screw 11 with respect to plate 4. Preferably, bone screw 11 is self-drilling and/or self-tapping.

While preferred embodiments and features of the present invention have been disclosed herein, it will be appreciated that numerous modifications and embodiments may be devised by those skilled in the art. It is intended that the appended claims cover all such modifications and embodiments as fall within the true spirit and scope of such claims and that the claims not be limited to or by such preferred embodiments or features.

What is claimed:

1. A bone plate defining a longitudinal axis and comprising:
    an upper surface;
    a bone contacting surface; and
    at least one hole extending through the upper and bone contacting surfaces for receiving a bone screw, the at least one hole including:
        a first portion defining a substantially circular outer periphery that defines a first center point, the first portion having a plurality of threads disposed thereon; and
        a second portion defining an elongated outer periphery that defines a second center point, wherein the elongated outer periphery is elongated in a direction substantially parallel to the longitudinal axis of the plate; wherein the second portion overlaps the first portion, and
        the first center point is spaced from the second center point along the longitudinal axis.

2. The bone plate of claim 1, wherein the elongated outer periphery is substantially elliptical.

3. The bone plate of claim 1, wherein the plurality of threads extends angle of greater than about 180° with respect to the first center point.

4. The bone plate of claim 1, wherein the threads taper inward in a direction from the upper surface towards the bone contacting surface.

5. The bone plate of claim 1, wherein:
    the substantially circular outer periphery defines a diameter (D);
    the elongated outer periphery defines a major axis (A) that is substantially parallel to the longitudinal axis of the bone plate, and a minor axis (B) that is substantially perpendicular to the major axis (A); and
    the first and second center points are spaced apart by a distance (X) that satisfies the condition:

$$X < A/2 + B/2.$$

6. The bone plate of claim 5, wherein the distance (X) satisfies the condition:

$$0.5(D/2+A/2)<X<1.0(D/2+A/2).$$

7. The bone plate of claim 5, wherein the diameter (D) satisfies the condition:

$$D<B.$$

8. The bone plate of claim 5, wherein the diameter (D) satisfies the condition:

$$0.75B \leq D \leq 0.95B.$$

9. The bone plate of claim 1, wherein:

the plurality of threads extends over a first angle at the upper surface;

the plurality of threads extends over a second angle at the bone contacting surface; and the first angle is different than the second angle.

10. The bone plate of claim 9, wherein the first angle is larger than the second angle.

11. The bone plate of claim 9, wherein the first angle is between about 200° and about 270°, and the second angle is between about 180° and about 230°.

12. The bone plate of claim 11, further comprising at least one bone screw having a screw-head that is configured and dimensioned to threadably engage the threads.

13. The bone plate of claim 1, wherein the second portion is configured and dimensioned to engage a substantially spherical screw-head and provide compression of fractured bone fragments.

14. The bone plate of claim 13, wherein the second portion includes a concave recess formed in the upper surface.

15. A bone plate having an upper surface and a bone contacting surface, e bone plate comprising:

a first section defining a first longitudinal axis;

a second section defining a second longitudinal axis, the second section connected to the first section with the second longitudinal axis disposed at an angle with respect to the first longitudinal axis; and at least one hole extending through the upper and bone contacting surfaces for receiving a bone screw, the at least one hole including:

a first portion defining a substantially circular outer periphery, the first portion having a plurality of threads disposed thereon; and a second portion overlapping the first portion, wherein the second portion defines an elongated outer periphery that is elongated along a direction substantially parallel to one of the first and second longitudinal axes.

16. The bone plate of claim 15, wherein:

the substantially circular outer periphery defines a first center point and a diameter (D);

the elongated outer periphery defines a second center point, a major axis (A) that is substantially parallel to the first longitudinal axis, and a minor axis (B) that is substantially perpendicular to the major axis (A); and the first and second center points are spaced apart by a distance (X) that satisfies the condition:

$$X<A/2+B/2.$$

17. The bone plate of claim 16, wherein the diameter (D) satisfies the condition:

$$D<B.$$

18. The bone plate of claim 15, wherein the threads taper inward in a direction from the upper surface towards the bone contacting surface.

19. The bone plate of claim 15, further comprising at least one bone screw having a screw-head that is configured and dimensioned to threadably engage the threads.

20. The bone plate of claim 15, wherein the second portion is configured and dimensioned to engage a substantially spherical screw-head and provide compression of fractured bone fragments.

21. The bone plate of claim 20, wherein the second portion includes a concave recess formed in the upper surface.

22. The bone plate of claim 15, wherein:

the first section is longer than the second section; and the at least one hole is disposed on the first section of the plate with the second portion longated in a direction substantially parallel to the first longitudinal axis, wherein the first portion of the hole is closer than the second portion of the hole to the second section of the plate.

23. The bone plate of claim 22, wherein the bone contacting surface of the first section is located in a first plane and the bone contacting surface of the second section is located in a second plane different from the first plane.

24. The bone plate of claim 22, wherein the plate is substantially L-shaped or T-shaped.

25. A bone plate comprising:

an upper surface;

a bone contacting surface; and at least one hole extending through the upper and bone contacting surfaces for receiving a bone screw, the at least one hole including:

a first portion defining a substantially circular outer periphery, the first portion outer periphery having a plurality of threads disposed thereon for engaging a threaded screw-head, the threads extending substantially completely around the circular outer periphery; and a second portion defining a substantially elliptical outer periphery, the second portion further defining a concave spherical recess in the upper surface of the bone plate;

wherein the first portion overlaps the second portion.

26. The bone plate of claim 25, wherein the first portion defines a first center point, and the plurality of threads extends over an angle of greater than about 180° with respect to the first center point.

27. The bone plate of claim 25, wherein the threads taper inward in a direction from the upper surface towards the bone contacting surface.

* * * * *

UNITED STATES PATENT AND TRADEMARK OFFICE
CERTIFICATE OF CORRECTION

PATENT NO. : 6,669,701 B2
DATED : April 29, 2004
INVENTOR(S) : Steiner et al.

It is certified that error appears in the above-identified patent and that said Letters Patent is hereby corrected as shown below:

<u>Title page,</u>
Item [75], Inventors, "Beatrice Steiner, Cham (CH); Markus Hehli, Frauenkirch (CH); Max Aebi, Montreal (CA); Thomas Steffen, Montreal (CA)" should be deleted and be replaced with -- Robert Frigg, Bettlach (CH) --.

Signed and Sealed this

Thirteenth Day of July, 2004

JON W. DUDAS
*Acting Director of the United States Patent and Trademark Office*